(12) United States Patent
Ollivierre et al.

(10) Patent No.: US 8,881,058 B2
(45) Date of Patent: Nov. 4, 2014

(54) SYSTEM AND METHOD FOR DISPLAYING OBJECTS IN A USER INTERFACE BASED ON A VISUAL ACUITY OF A VIEWER

(76) Inventors: Arthur Austin Ollivierre, San Francisco, CA (US); Robert Michael DiNapoli, San Francisco, CA (US)

( * ) Notice: Subject to any disclaimer, the term of this patent is extended or adjusted under 35 U.S.C. 154(b) by 0 days.

(21) Appl. No.: 13/078,661

(22) Filed: Apr. 1, 2011

(65) Prior Publication Data

US 2012/0254779 A1  Oct. 4, 2012

(51) Int. Cl.
| | | |
|---|---|---|
| *G06F 3/048* | (2013.01) | |
| *A61B 3/00* | (2006.01) | |
| *G06F 3/0489* | (2013.01) | |
| *A61B 3/032* | (2006.01) | |
| *G06F 9/44* | (2006.01) | |

(52) U.S. Cl.
CPC .......... *A61B 3/0041* (2013.01); *G06F 3/04897* (2013.01); *A61B 3/032* (2013.01); *G06F 9/4443* (2013.01); *G06F 2203/04806* (2013.01)
USPC ........... 715/815; 715/764; 715/853; 715/246; 345/633

(58) Field of Classification Search
CPC .............................. G06F 3/0482; G06F 3/0481
USPC ............................ 715/764, 853, 246; 345/633
See application file for complete search history.

(56) References Cited

U.S. PATENT DOCUMENTS

| | | | |
|---|---|---|---|
| 4,884,199 A | | 11/1989 | Boothroyd et al. |
| 4,967,372 A | * | 10/1990 | Feldman ........................ 715/203 |
| 5,504,853 A | * | 4/1996 | Schuur et al. ................. 715/853 |
| 5,640,176 A | * | 6/1997 | Mundt et al. .................. 715/839 |
| 5,724,074 A | * | 3/1998 | Chainani et al. .............. 345/474 |
| 5,835,923 A | * | 11/1998 | Shibata et al. ................. 715/246 |
| 5,903,254 A | * | 5/1999 | Mundt et al. .................. 715/846 |
| 6,046,745 A | * | 4/2000 | Moriya et al. ................ 345/420 |
| 6,061,666 A | * | 5/2000 | Do et al. ......................... 705/43 |
| 6,118,442 A | * | 9/2000 | Tanigawa ...................... 715/719 |
| 6,169,535 B1 | * | 1/2001 | Lee ................................. 345/660 |
| 6,181,342 B1 | * | 1/2001 | Niblack ......................... 345/635 |
| 6,195,082 B1 | * | 2/2001 | May et al. ...................... 345/161 |
| 6,233,591 B1 | * | 5/2001 | Sherman et al. .............. 715/205 |

(Continued)

FOREIGN PATENT DOCUMENTS

WO   WO-2012135368 A1   10/2012

OTHER PUBLICATIONS

Windows 7 ClearType Text Tuner Makes Text Appear More Sharp and Clear—Jul. 27, 2009.*

(Continued)

*Primary Examiner* — Doon Chow
*Assistant Examiner* — David Choi
(74) *Attorney, Agent, or Firm* — Welsh Flaxman & Gitler LLC

(57) ABSTRACT

A system, a computer readable storage medium including programs, and a computer-implemented method for displaying objects in a graphical user interface of a device are described. A vision test is presented in the graphical user interface of the device, the vision test including vision test objects used to test a visual acuity level of a user of the device. Input is received from the user identifying the user's ability to see at least one vision test object in the vision test. Display settings corresponding to the input received from the user are identified. Objects in the graphical user interface are displayed based on the display settings.

24 Claims, 11 Drawing Sheets

(56) References Cited

U.S. PATENT DOCUMENTS

| | | | |
|---|---|---|---|
| 6,386,707 | B1 | 5/2002 | Pellicano |
| 6,850,245 | B1* | 2/2005 | Murashita et al. ............ 345/589 |
| 7,198,369 | B2* | 4/2007 | Chen et al. .................... 351/246 |
| 7,843,471 | B2* | 11/2010 | Doan et al. .................... 345/633 |
| 7,971,155 | B1* | 6/2011 | Yoon ............................. 715/843 |
| 8,345,338 | B2* | 1/2013 | Jeong et al. ................. 359/222.1 |
| 2002/0035560 | A1* | 3/2002 | Sone ................................ 707/5 |
| 2003/0002069 | A1 | 1/2003 | Bhogal et al. |
| 2004/0119714 | A1* | 6/2004 | Everett et al. ................. 345/471 |
| 2004/0119715 | A1* | 6/2004 | Everett et al. ................. 345/471 |
| 2006/0280338 | A1* | 12/2006 | Rabb ............................ 382/114 |
| 2007/0150829 | A1* | 6/2007 | Eschbach et al. ............. 715/781 |
| 2007/0159470 | A1* | 7/2007 | Jeng et al. .................... 345/204 |
| 2007/0211047 | A1* | 9/2007 | Doan et al. ................... 345/419 |
| 2007/0236656 | A1* | 10/2007 | Jeong et al. .................. 351/163 |
| 2008/0034316 | A1* | 2/2008 | Thoresson ................... 715/781 |
| 2008/0048026 | A1 | 2/2008 | Gangi |
| 2008/0242950 | A1* | 10/2008 | Jung et al. .................... 600/300 |
| 2009/0109468 | A1 | 4/2009 | Barclay et al. |
| 2010/0103197 | A1* | 4/2010 | Liu ................................ 345/660 |
| 2010/0125561 | A1* | 5/2010 | Leuthardt et al. ............. 707/706 |
| 2011/0093438 | A1* | 4/2011 | Poulsen ........................ 707/661 |
| 2011/0149059 | A1* | 6/2011 | Alberth ........................... 348/77 |
| 2011/0157180 | A1* | 6/2011 | Burger et al. ................. 345/428 |
| 2011/0164188 | A1* | 7/2011 | Karaoguz et al. ............. 348/734 |
| 2012/0016678 | A1* | 1/2012 | Gruber et al. ................. 704/275 |
| 2012/0246678 | A1* | 9/2012 | Barksdale ....................... 725/37 |
| 2012/0250039 | A1 | 10/2012 | Ollivierre et al. |
| 2012/0254779 | A1* | 10/2012 | Ollivierre et al. ............. 715/764 |
| 2013/0055164 | A1* | 2/2013 | Bergsbjork ................... 715/845 |

OTHER PUBLICATIONS

"U.S. Appl. No. 13/167,234, Non Final Office Action mailed Nov. 8, 2012", 12 pgs.

"International Application Serial No. PCT/US2012/030984, International Search Report mailed Jun. 20, 2012", 3 pgs.

"International Application Serial No. PCT/US2012/030984, Written Opinion mailed Jun. 20, 2012", 7 pgs.

"U.S. Appl. No. 13/167,234, Response filed May 7, 2013 to Non Final Office Action mailed Nov. 8, 2012", 11 pgs.

"U.S. Appl. No. 13/167,234, Final Office Action mailed Oct. 10, 2013", 12 pgs.

"U.S. Appl. No. 13/167,234, Response filed May 14, 2013 to Notice of Non Compliant Amendment mailed May 10, 2013", 8 pgs.

* cited by examiner

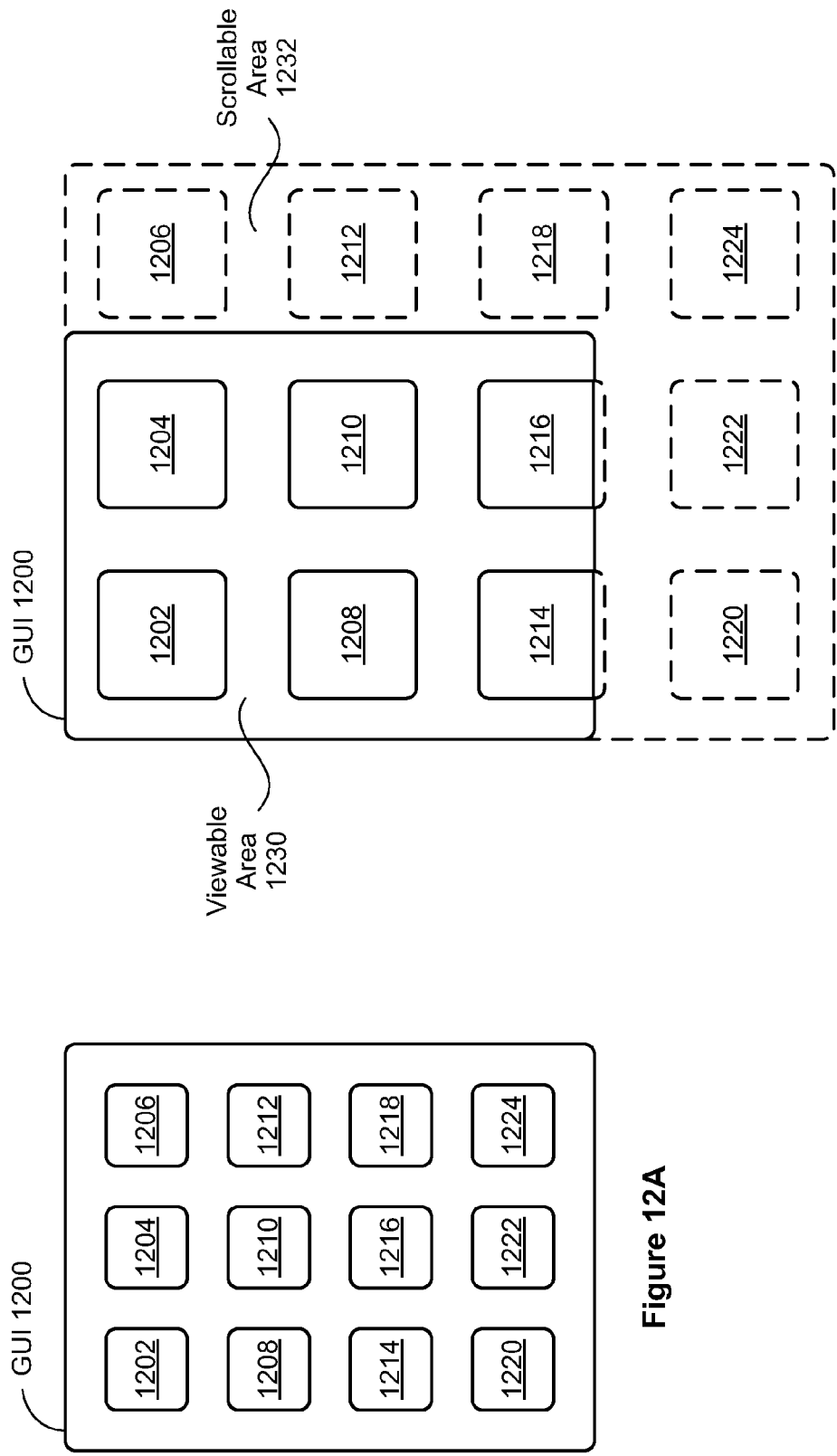

SYSTEM AND METHOD FOR DISPLAYING OBJECTS IN A USER INTERFACE BASED ON A VISUAL ACUITY OF A VIEWER

TECHNICAL FIELD

The disclosed embodiments relate generally to displaying objects in a graphical user interface based on a visual acuity of a viewer.

BACKGROUND

Many users of electronic devices have issues with vision that inhibit the users from being able to see objects displayed on electronic devices. Glasses or contact lenses may allow users that are nearsighted or farsighted to see these objects. However, users may not be wearing their glasses or contact lenses when using electronic devices. Furthermore, some users may have vision issues that are not correctable using glasses or contact lenses. Although some electronic devices allow users to change the display settings of these electronic devices, the users still need to navigate the user interface of the electronic device in order to change the display settings. For example, in the Windows operating system, a user must click on the "Start" button, move the cursor to the "Settings" menu item, select "Control Panel", double click on the "Display Settings" icon, click on the "Settings" tab of the "Display Properties" window, and slide a resolution slider to select a desired resolution level. During this process, if the user cannot see the text and/or icons, the user may not be able to navigate through a series of screens or graphical user interfaces to change the display settings.

BRIEF DESCRIPTION OF THE DRAWINGS

The embodiments disclosed in the present disclosure are illustrated by way of example, and not by way of limitation, in the figures of the accompanying drawings. Like reference numerals refer to corresponding parts throughout the drawings.

FIG. 12A illustrates objects displayed in an example graphical user interface, according to some embodiments.

FIG. 12B illustrates the objects displayed in the example graphical user interface of FIG. 12A after display settings for the graphical user interface have been modified, according to some embodiments.

DESCRIPTION OF EXAMPLE EMBODIMENTS

The description that follows includes illustrative systems, methods, techniques, instruction sequences, and computing machine program products that embody illustrative embodiments. In the following description, for purposes of explanation, numerous specific details are set forth in order to provide an understanding of various embodiments of the inventive subject matter. It will be evident, however, to those skilled in the art that embodiments of the inventive subject matter may be practiced without these specific details. In general, well-known instruction instances, protocols, structures and techniques have not been shown in detail.

The example embodiments described herein provide techniques for displaying objects in a graphical user interface based on a visual acuity of a viewer.

In some embodiments, a vision test is presented in the graphical user interface of the device, where the vision test includes vision test objects used to test a visual acuity level of a user of the device. Input is then received from the user identifying the user's ability to see at least one vision test object in the vision test. Next, display settings corresponding to the input received from the user are identified. Objects are then displayed in the graphical user interface based on the display settings. These embodiments are described in more detail below.

Figure 1A:
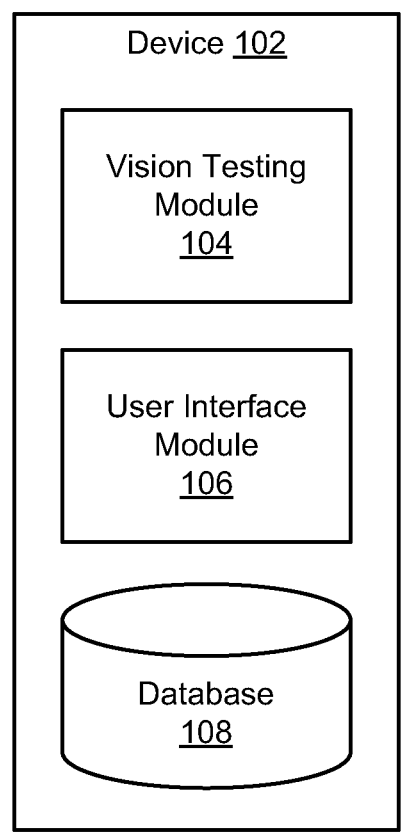
FIG. 1A is a block diagram illustrating a device, according to some embodiments.

FIG. 1A is a block diagram illustrating a device 102, according to some embodiments. The device 102 may include any electronic device coupled to a display device (e.g., a monitor, a television) including, but is not limited to, a desktop computer system, a laptop computer system, a server, a mobile phone, a smart phone, a personal digital assistant (PDA), a gaming console, a portable gaming console, a set top box, a camera, a printer, a television set, or the like.

The device 102 includes a vision testing module 104, a user interface module 106, and a database 108. The vision testing module 104 is configured to determine a visual acuity of a user of the device 102. The visual acuity of the user is the ability of the user of the device 102 to see objects displayed on a display device (e.g., a monitor) of the device 102. The visual acuity of the user may be determined by an optometrist or an ophthalmologist using a Snellen Test. The Snellen test includes block letters of varying sizes displayed at a predetermined distance (e.g., 20 feet from the user). The ability of a user to read a particular line of letters indicates the visual acuity of the user. However, other factors may influence the ability of the user to see objects displayed on the display device of the device 102. For example, the dimensions and the resolution of the display device may affect the ability of the user to see objects displayed on the display device. The user may be able to see objects displayed on a large display at a low resolution because the objects may be large enough to be seen by the user. However, the user may not be able to see objects displayed on a large display at a high resolution because the individual objects may be too small to be seen by the user. Similarly, the user may not be able to see objects displayed on a small display at a high resolution because the objects may be too small to be seen by the user. However, the user may be able to see objects displayed on a small display at a low resolution because the objects may be large enough to be seen by the user.

The user interface module 106 is configured to display objects in a graphical user interface of a display device of the device 102 based on display settings. The database 108 stores vision test objects, reference visual acuity levels, reference display settings, predetermined viewing distances of display devices (e.g., based dimensions and resolution of the display devices), scaling factors for objects corresponding to the reference visual acuity levels, and user profiles for users of the device 102 that include a visual acuity level and/or display settings for the user (or a plurality of users) with respect to the device 102.

Figure 1B:
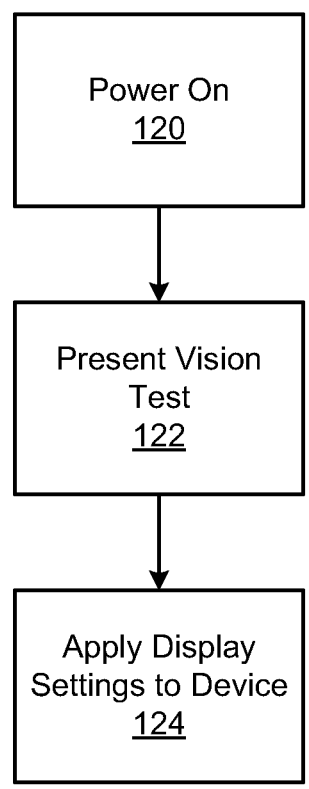
FIG. 1B illustrates an example method to customize display settings of a display screen of an electronic device (e.g., during a boot-up sequence of the device), according to some embodiments.

FIG. 1B illustrates an example method to customize display settings of a display screen of an electronic device (e.g., during a boot-up sequence) of the device, according to some embodiments. In some embodiments, after the device 102 is powered on (operation 120), the vision testing module 104 is executed and a vision test is presented (operation 122) to the user. In these embodiments, the vision test is administered each time the device 102 is powered on. In some embodiments, after the device 102 is powered on, the vision testing module 104 is executed and a vision test is administered to the user when requested by the user. Display settings that are identified as a result of the vision test are applied to the device (operation 124). In an example embodiment, the display settings are applied to applications running on the device. It is to be appreciated that the method may be performed at any time before, during and after the device boots up. In an example embodiment, the method allows a user who may have visual impairment to adjust or modify display setting on the devices even though the user is unable to read or adequately perceive images or text displayed on the display screen of the display device.

Figure 2:
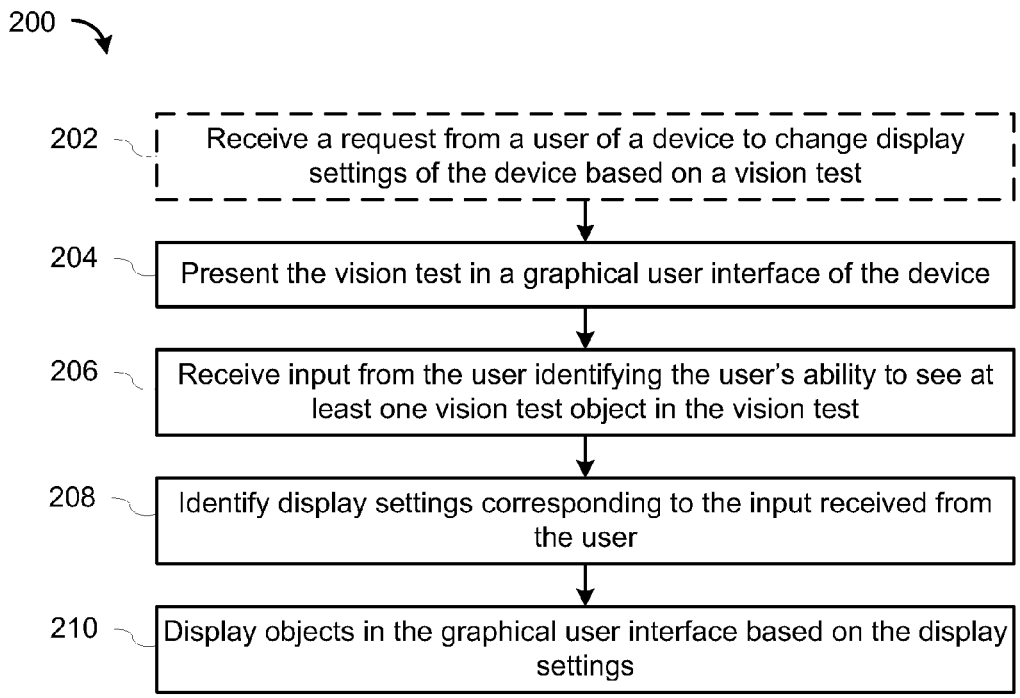
FIG. 2 is a flowchart of a method for displaying objects in a graphical user interface of a device, according to some embodiments.

FIG. 2 is a flowchart of a method 200 for displaying objects in a graphical user interface of the device 102, according to some embodiments. In some embodiments, the vision testing module 104 receives (operation 202) a request from a user of the device 102 to change display settings of the device 102 based on a vision test. The request may include a voice-activated request, a predetermined key sequence, and/or a predetermined gesture in the graphical user interface of the device 102. Note that operation 202 may be optional. For example, the vision testing module 104 may always present the vision test to the user of the device 102 if the device 102 is a publically-accessible device (e.g., a kiosk, a public computer system) or on the first login of the user on the device 102.

Figure 10:
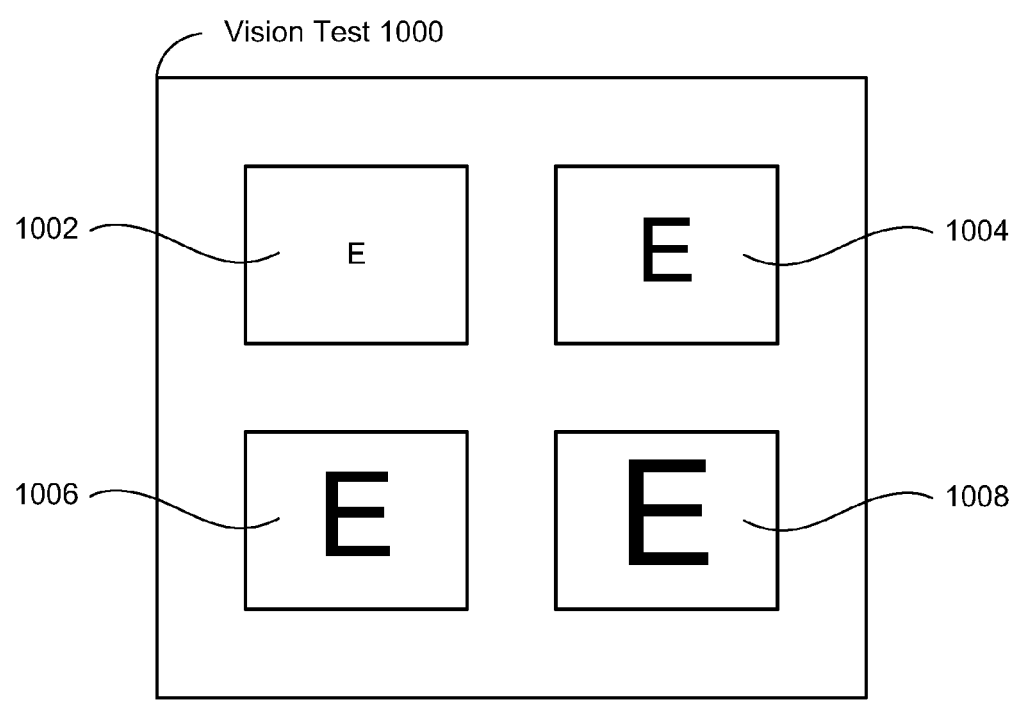
FIG. 10 illustrates an example vision test, according to some embodiments.
Figure 11:
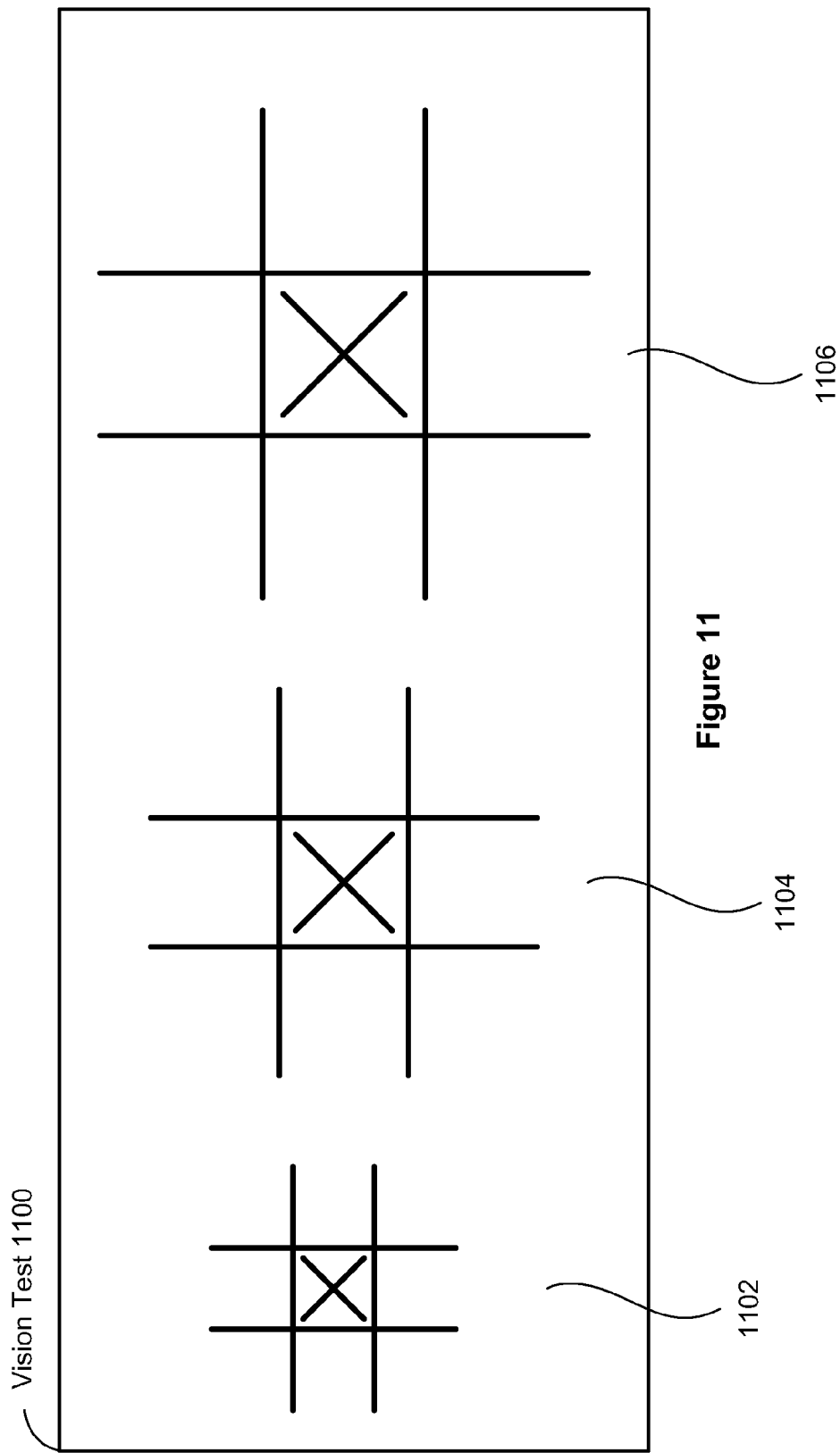
FIG. 11 illustrates another example vision test, according to some embodiments.

The vision testing module 104 presents (operation 204) the vision test in the graphical user interface of the device 102. Operation 204 is described in more detail by way of example with reference to FIG. 3. In some embodiments, the vision test includes vision test objects used to test a visual acuity level of a user of the device 102. Attention is now directed to FIGS. 10 and 11, which illustrate example vision tests, according to some embodiments. FIG. 10 illustrates a vision test 1000 that includes vision test objects 1002, 1004, 1006, and 1008. As illustrated in FIG. 10, the vision test objects 1002, 1004, 1006, and 1008 are shown by way of example to include the letter "E" having varying sizes. During the vision test, the user of the device 102 may be asked to select the smallest letter "E" that the user can see. For example, if the user is unable to see letter "E" represented by the vision test object 1002 but is able to see letter "E" represented by the vision test object 1004, the smallest letter that the user can see would be the letter "E" corresponding to test object 1004.

FIG. 11 illustrates a vision test 1100 that includes vision test objects 1102, 1104, and 1106. As illustrated in FIG. 11, the vision test objects 1102, 1104, and 1106 include a "Tic-Tac-Toe" pattern including an "X" in the center of the pattern. During the vision test, the user of the device 102 may be asked to select the smallest "Tic-Tac-Toe" pattern that the user can see where the horizontal and vertical lines appear as straight lines.

In some embodiments, while presenting the vision test to the user of the device 102, the vision testing module 104 prompts the user for input identifying the user's ability to see at least one vision test object in the vision test. In some embodiments, the vision testing module 104 generates visual prompts (e.g., text). In some embodiments, the vision testing module 104 generates audio prompts (e.g., voice prompts).

In some embodiments, the vision test includes a sequence of vision test objects that are displayed to the user. The sequence of vision test objects may include vision test objects from different types of vision test techniques (e.g., the vision test 1000, the vision test 1100). Alternatively, or additionally, the sequence of vision test objects may be used to obtain a more precise level of visual acuity for the user. For example, the vision testing module 104 may present a first vision test object and may ask the user whether the user can see the first vision test object. Based on the user's response, the vision testing module 104 presents an appropriate second vision test object. The vision testing module 104 repeats the process until the level of visual acuity is determined.

Returning to FIG. 2, the vision testing module 104 receives (operation 206) input from the user identifying the user's ability to see at least one vision test object in the vision test. For example, the vision testing module 104 may receive input from the user indicating that the smallest letter "E" that the user can see is the letter "E" corresponding to the vision test object 1004. Similarly, the vision testing module 104 may receive input from the user indicating that smallest "Tic-Tac-Toe" pattern that the user can see where the horizontal and vertical lines appear as straight lines is the "Tic-Tac-Toe" pattern corresponding to the vision test object 1104. It is however to be noted that this disclosure is not limited to the example vision test illustrated in FIGS. 10 and 11 and that other example embodiments may include other vision tests.

The vision testing module 104 identifies (operation 208) display settings corresponding to the input received from the user (e.g., from a touch screen on a mobile device, computer or other electronic device including a display screen). In some embodiments, the display settings include one or more of a size of an object, a shape of the object, a color of the object, a brightness of the object, a contrast level of the object, and a location of the object. Operation 208 is described in more detail by way of example with reference to FIG. 5.

The user interface module 106 displays (operation 210) objects in the graphical user interface based on the display settings. The objects may include icons and/or text. Thus, as described above, objects are displayed in the graphical user interface using the display settings corresponding to a visual acuity level of a user without requiring the user to navigate through menus. Operation 210 is described in more detail by way of example with reference to FIG. 6.

Figure 3:
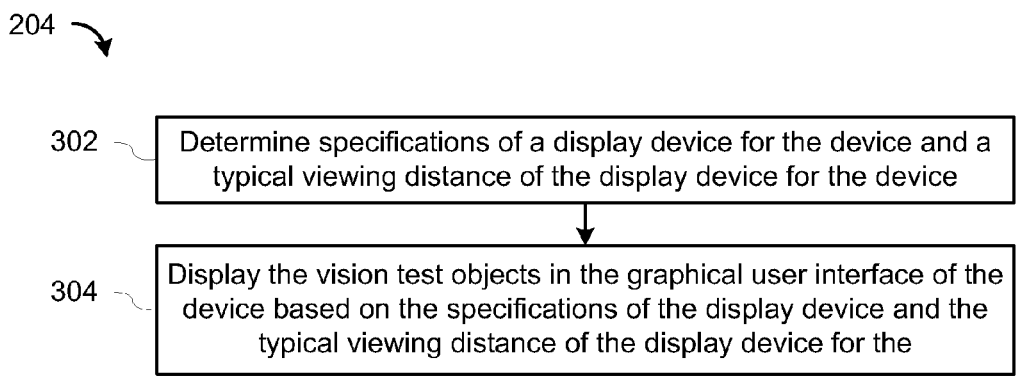
FIG. 3 is a flowchart of a method for presenting a vision test in a graphical user interface of a device, according to some embodiments.

FIG. 3 is a flowchart of a method for presenting (operation 204) a vision test in the graphical user interface of the device 102, according to some embodiments. The vision testing module 104 determines (operation 302) specifications of a display device for the device 102 and a predetermined viewing distance of the display device for the device 102. In some embodiments, the specifications of the display device include physical dimensions of the display device and a resolution of the display device.

Figure 4:
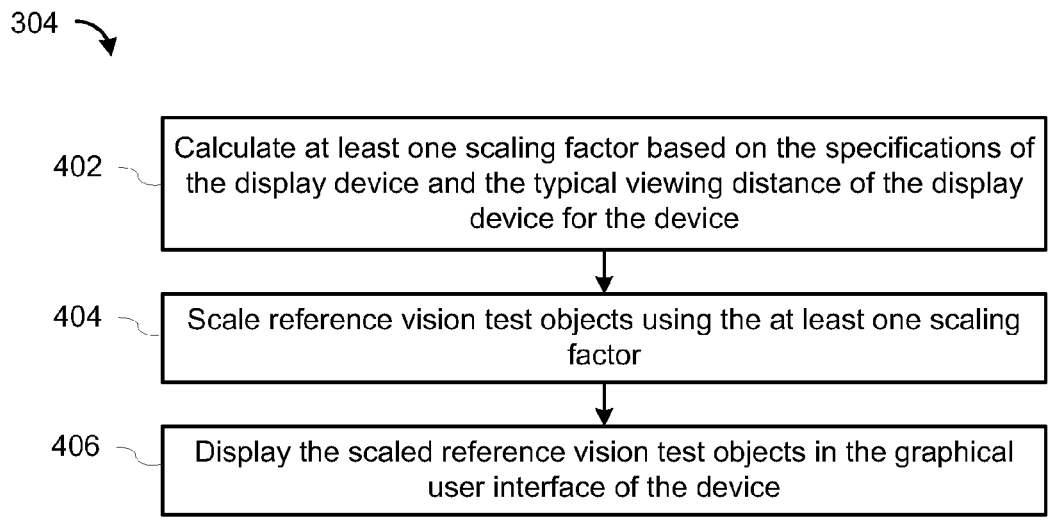
FIG. 4 is a flowchart of a method for displaying vision test objects in a graphical user interface of a device, according to some embodiments.

The user interface module 106 displays (operation 304) the vision test objects in the graphical user interface of the device 102 based on the specifications of the display device and the predetermined viewing distance of the display device for the device 102. For example, to provide a vision test comparable to the Snellen test, the user interface module 106 may scale the letters in the Snellen test to account for the dimensions of the display device, the resolution of the display device, and/or the predetermined viewing distance of the display device. Operation 304 is described in more detail with respect to FIG. 4, which is a flowchart of a method for displaying (operation 304) vision test objects in the graphical user interface of the device 102, according to some embodiments. The vision testing module 104 calculates (operation 402) at least one scaling factor based on the specifications of the display device and the predetermined viewing distance of the display device for the device 102. The vision testing module 104 scales (operation 404) reference vision test objects using the at least one scaling factor. In some embodiments, each reference vision test object corresponds to a reference visual acuity level. The vision testing module 104 displays (operation 406) the scaled reference vision test objects in the graphical user interface of the device 102.

Figure 5:
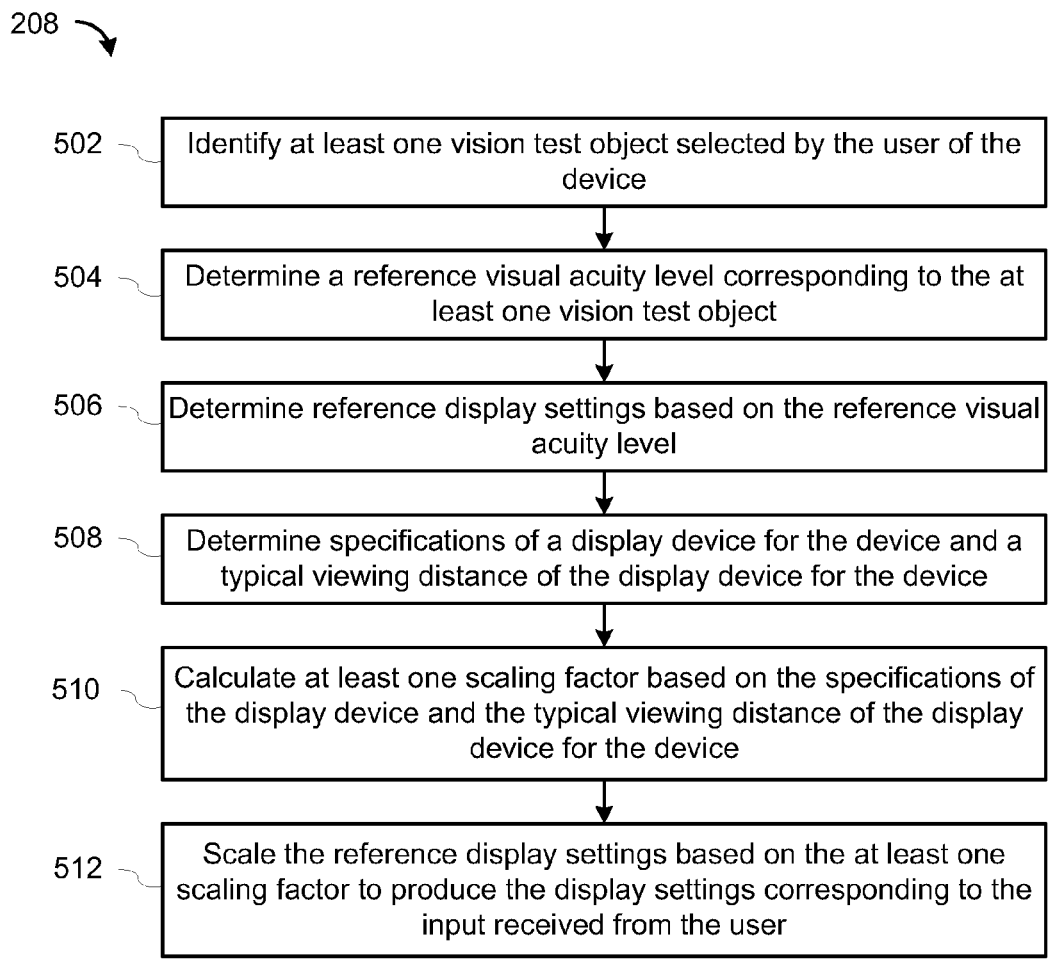
FIG. 5 is a flowchart of a method for identifying display settings corresponding to input received from a user, according to some embodiments.

FIG. 5 is a flowchart of a method for identifying (operation 208) display settings corresponding to input received from a user, according to some embodiments. The vision testing module 104 identifies (operation 502) at least one vision test object selected by the user of the device 102. For example, the vision testing module 104 may identify that the user selected the vision test object 1002.

The vision testing module 104 determines (operation 504) a reference visual acuity level corresponding to the at least one vision test object. Note that a reference visual acuity level may be a standard (or normalized) visual acuity level. For example, the reference visual acuity level may correspond to a Snellen fraction (e.g., 20/40, 20/20). The reference visual acuity level may be independent of the dimensions of the display device, the resolution of the display device, and the predetermined viewing distance of the display device.

In some embodiments, the user enters the reference visual acuity level of the user. For example, if the user has a visual acuity level of 20/40, the user may enter this visual acuity level into a text field of the vision test. In these embodiments, the operations 502 and 504 are not performed.

The vision testing module 104 determines (operation 506) reference display settings based on the reference visual acuity level. The reference display settings may be a standard (or normalized) display setting based on the reference visual acuity level and a reference display device. For example, the reference display setting corresponding to a Snellen fraction 20/20 may indicate that a reference display device that is a 23" widescreen display device viewed 24" away from the user may be set to a resolution of 2048×1152. Similarly, the reference display setting corresponding to a Snellen fraction 20/40 may indicate that the reference display device (e.g., the 23" widescreen display device) viewed 24" away from the user may be set to a resolution of 1280×720. The reference display settings are used to scale up or scale down the size of objects displayed on the display device of the device 102. The mapping of the scale factors (e.g., based on the dimensions of the display device, the current resolution of the display device, and the distance of the display device to the user's eye) for a particular display device (or class of display devices) to a reference display setting may be stored in the database 108.

The vision testing module 104 determines (operation 508) specifications of a display device for the device 102 and a predetermined viewing distance of the display device for the device 102. For example, the vision testing module 104 may determine the dimensions and the current resolution of the display device for the device 102.

Since the dimensions, the current resolution, and the predetermined viewing distance (e.g., the typical viewing distance) of the display device for the device 102 may affect the vision test being administered to the user, the vision testing module 104 calculates (510) at least one scaling factor based on the specifications of the display device and the predetermined viewing distance of the display device for the device 102. For example, a mobile phone that is 2 inches by 4 inches, has a resolution of 960×640, and is typically viewed at 12 inches from the user's eye may have a scaling factor of 2.

The vision testing module 104 scales (operation 512) the reference display settings based on the at least one scaling factor to produce the display settings corresponding to the input received from the user. For example, assume that the reference visual acuity level is 20/40 and the display device is the mobile phone described above. Accordingly, the scaling factor is 2 and resolution of the mobile phone is decreased by a factor of 2 (e.g., to increase the size of objects displayed). Note that scale factor accounts for the dimensions of the display device, the resolution of the display device, and the predetermined viewing distance of the display device relative to the reference display device.

Figure 6:
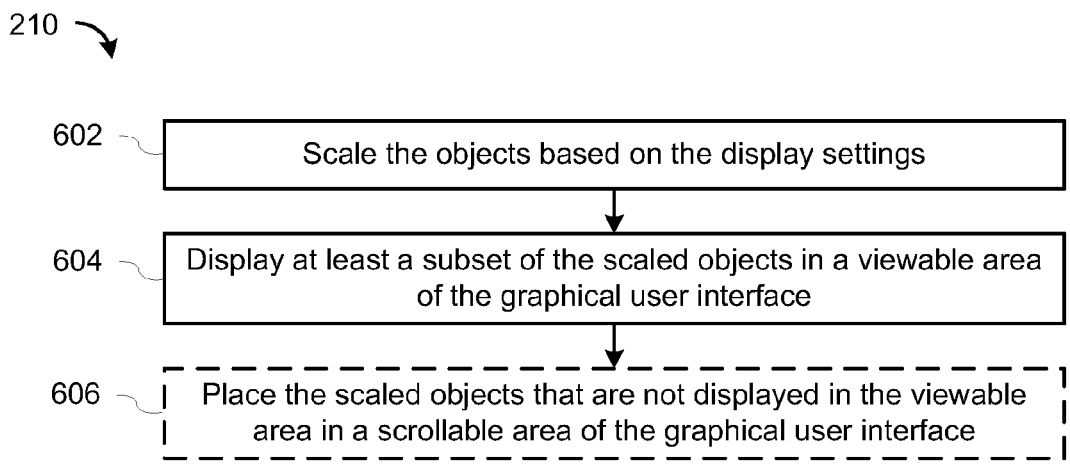
FIG. 6 is a flowchart of a method for displaying objects in a graphical user interface based on the display settings, according to some embodiments.

FIG. 6 is a flowchart of a method for displaying (operation 210) objects in the graphical user interface based on the display settings, according to some embodiments. The user interface module 106 scales (operation 602) the objects based on the display setting and displays (operation 604) at least a subset of the scaled objects in a viewable area of the graphical user interface. In some embodiments, the user interface module 106 places (operation 606) the scaled objects that are not displayed in the viewable area in a scrollable area of the graphical user interface. For example, FIG. 12A illustrates example objects 1202-1224 displayed in an example graphical user interface (GUI) 1200, according to some embodiments. After scaling the objects, the user interface module 106 may only display the example objects 1202, 1204, 1208, 1210, 1214, and 1216 in a viewable area 1230 of the GUI 1200, as illustrated in FIG. 12B. The example objects 1206, 1212, 1218, 1220, 1222, and 1224 may be placed in the scrollable area 1232 of the GUI 1200.

Figure 7:
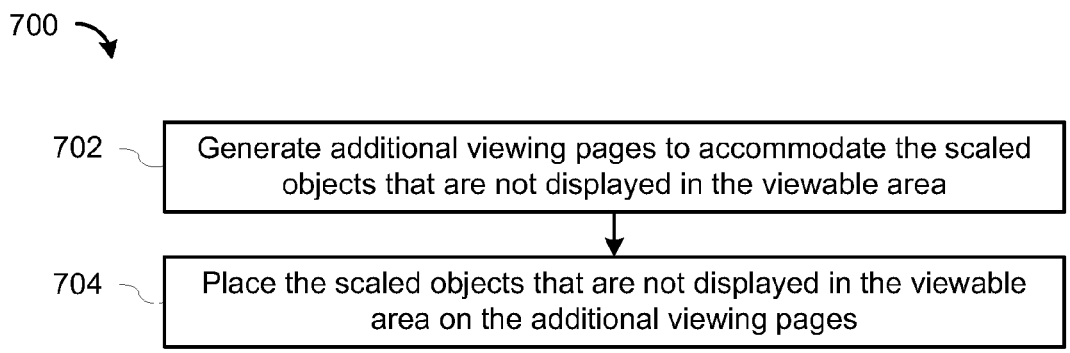
FIG. 7 is a flowchart of a method for generating additional viewing pages to display objects not displayed in a viewable area of a graphical user interface, according to some embodiments.
Figure 12C:
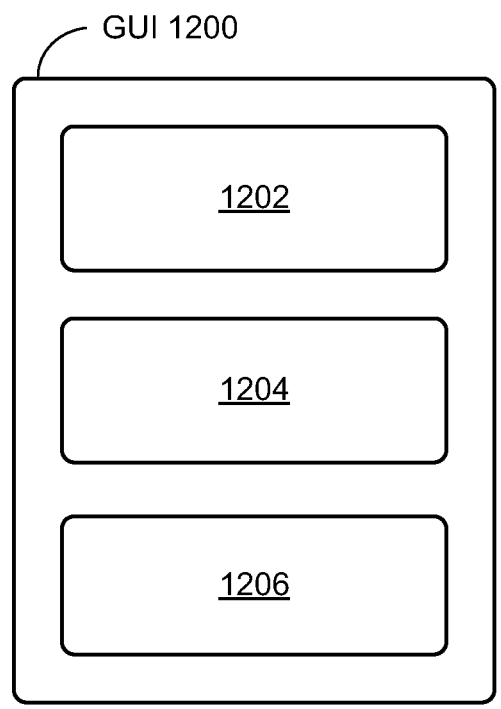
FIG. 12C illustrates the objects displayed in the example graphical user interface of FIG. 12A after display settings for the graphical user interface have been modified, according to some embodiments.

On mobile devices, the GUI may include "pages" that the user may scroll through to access objects not displayed in the viewable area of the GUI. When objects are scaled to increase their size, the number of pages typically increases because the number of objects that can be displayed on a particular viewing page decreases. FIG. 7 is a flowchart of a method 700 for generating additional viewing pages to display objects not displayed in a viewable area of the graphical user interface, according to some embodiments. The user interface module 106 generates (operation 702) additional viewing pages to accommodate the scaled objects that are not displayed in the viewable area. The user interface module 106 places (operation 704) the scaled objects that are not displayed in the viewable area on the additional viewing pages. FIG. 12C illustrates the example objects 1202, 1204, and 1206 after being scaled to increase the size of the objects displayed on a viewing page of the GUI 1200. Due to the increased size of the objects, only three objects are displayed on the viewing page of the GUI 1200. The other objects are placed on other viewing pages. Assuming that the unscaled versions of the example objects 1202-1224 fit on one viewing page, the user interface module creates three additional viewing pages to accommodate the other objects not displayed.

Figure 8:
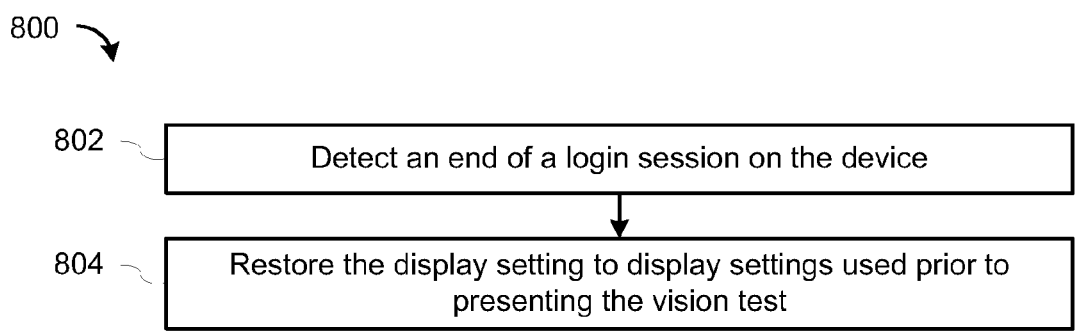
FIG. 8 is a flowchart of a method for restoring display settings at the end of a login session, according to some embodiments.

On publically-accessible devices (e.g., public computer systems, kiosks), it may be desirable to restore the display settings to a standard display setting (e.g., a display setting of the device 102 prior to the administration of the vision test). FIG. 8 is a flowchart of a method 800 for restoring display settings at the end of a login session, according to some embodiments. The vision testing module 104 detects (operation 802) an end of a login session on the device and restores (804) the display setting to display settings used prior to presenting the vision test.

Figure 9:
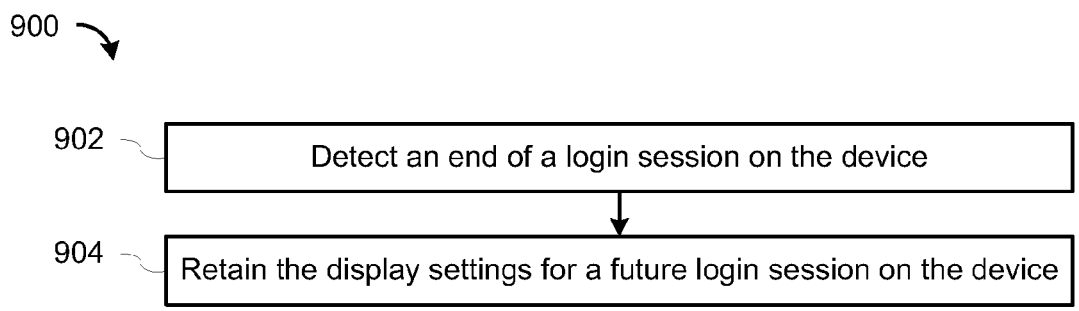
FIG. 9 is a flowchart of a method for retaining display settings between login sessions, according to some embodiments.

On personal devices, it may be desirable to retain display settings between login sessions. FIG. 9 is a flowchart of a method 900 for retaining display settings between login sessions, according to some embodiments. The vision testing module 104 detects (operation 902) an end of a login session on the device and retains (operation 904) the display settings for a future login session on the device. For example, the display setting may be saved in persistent memory of an electronic device. Upon subsequently login by the same user, the associated display setting are retrieved from memory and used to configure the display.

Example Electronic Device/Machine

Figure 13:
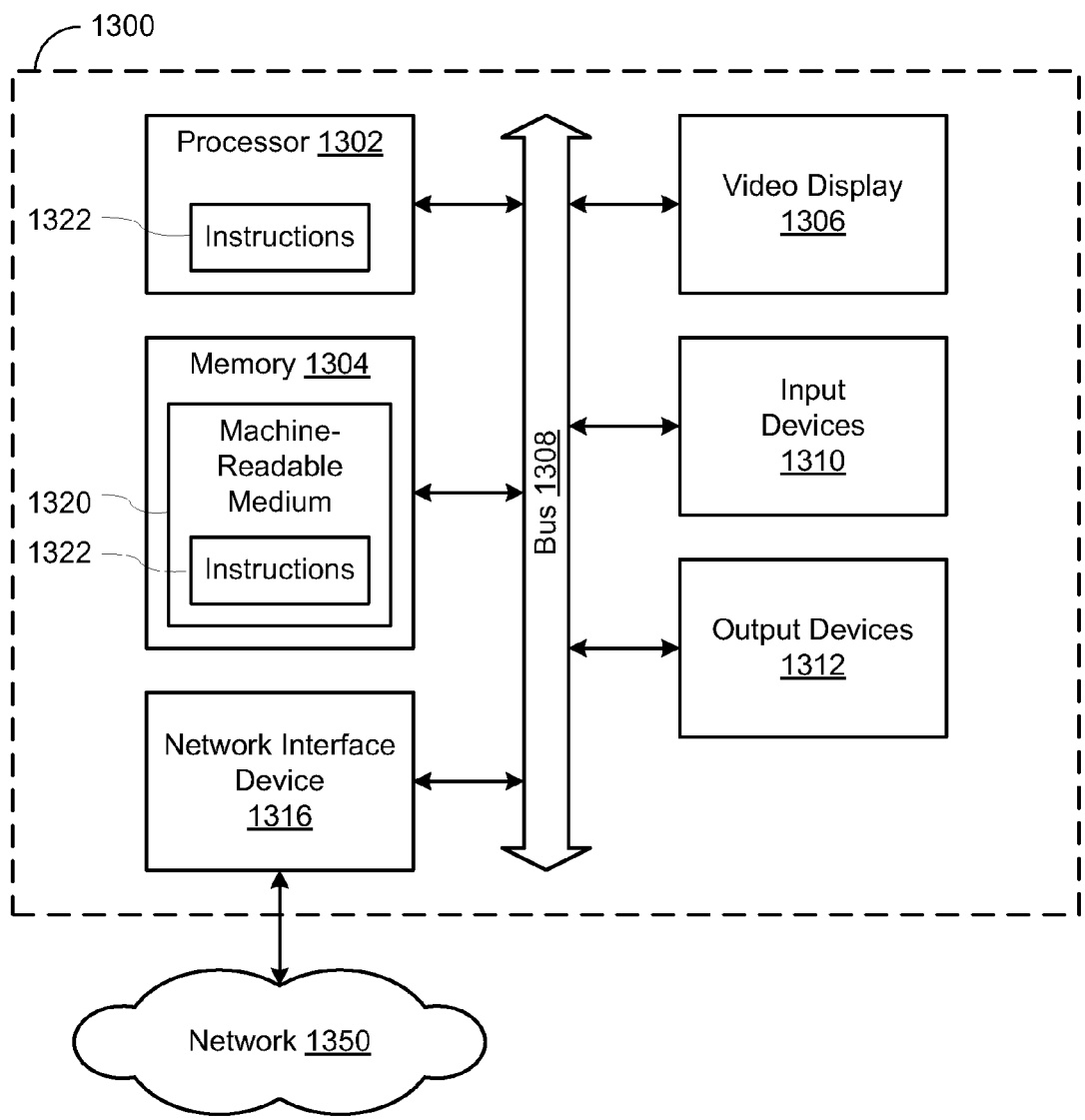
FIG. 13 is a block diagram illustrating an example machine for performing the methodologies described herein, according to some embodiments.

FIG. 13 depicts a block diagram of a machine in the example form of a computer system 1300 within which may be executed a set of instructions for causing the machine to perform any one or more of the methodologies discussed herein. In alternative embodiments, the machine operates as a standalone device or may be connected (e.g., networked) to other machines. In a networked deployment, the machine may operate in the capacity of a server or a client machine in a server-client network environment or as a peer machine in a peer-to-peer (or distributed) network environment. The computer system 1300 may include, but is not limited to, a desktop computer system, a laptop computer system, a server, a mobile phone, a smart phone, a personal digital assistant (PDA), a gaming console, a portable gaming console, a set top box, a camera, a printer, a television set, or any other electronic device.

The machine is capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example of the computer system 1300 includes a processor 1302 (e.g., a central processing unit (CPU), a graphics processing unit (GPU) or both), and memory 1304, which communicate with each other via bus 1308. Memory 1304 includes volatile memory devices (e.g., DRAM, SRAM, DDR RAM, or other volatile solid state memory devices), non-volatile memory devices (e.g., magnetic disk memory devices, optical disk memory devices, flash memory devices, tape drives, or other non-volatile solid state memory devices), or a combination thereof. Memory 1304 may optionally include one or more storage devices remotely located from the computer system 1300. The computer system 1300 may further include a video display unit 1306 (e.g., a plasma display, a liquid crystal display (LCD) or a cathode ray tube (CRT)). The computer system 1300 also includes input devices 1310 (e.g., keyboard, mouse, trackball, touchscreen display, etc.), output devices 1312 (e.g., speakers), and a network interface device 1316. The aforementioned components of the computer system 1300 may be located within a single housing or case (e.g., as depicted by the dashed lines in FIG. 13). Alternatively, a subset of the components may be located outside of the housing. For example, the video display unit 1306, the input devices 1310, and the output devices 1312 may exist outside of the housing, but be coupled to the bus 1308 via external ports or connectors accessible on the outside of the housing.

Memory 1304 includes a machine-readable medium 1320 on which is stored one or more sets of data structures and instructions 1322 (e.g., software) embodying or utilized by any one or more of the methodologies or functions described herein. The one or more sets of data structures may store data. Note that a machine-readable medium refers to a storage medium that is readable by a machine (e.g., a computer-readable storage medium). The data structures and instructions 1322 may also reside, completely or at least partially, within memory 1304 and/or within the processor 1302 during execution thereof by computer system 1300, with memory 1304 and processor 1302 also constituting machine-readable, tangible media.

The data structures and instructions 1322 may further be transmitted or received over a network 1350 via network interface device 1316 utilizing any one of a number of well-known transfer protocols (e.g., HyperText Transfer Protocol (HTTP)). Network 1350 can generally include any type of wired or wireless communication channel capable of coupling together computing nodes (e.g., the computer system 1300). This includes, but is not limited to, a local area network (LAN), a wide area network (WAN), or a combination of networks. In some embodiments, network 1350 includes the Internet.

Certain embodiments are described herein as including logic or a number of components, modules, or mechanisms. Modules may constitute either software modules (e.g., code and/or instructions embodied on a machine-readable medium or in a transmission signal) or hardware modules. A hardware module is a tangible unit capable of performing certain operations and may be configured or arranged in a certain manner. In example embodiments, one or more computer systems (e.g., the computer system 1300) or one or more hardware modules of a computer system (e.g., a processor 1302 or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a processor 1302 or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired) or temporarily configured (e.g., programmed) to operate in a certain manner and/or to perform certain operations described herein. Considering embodiments in which hardware modules are temporarily configured (e.g., programmed), each of the hardware modules need not be configured or instantiated at any one instance in time. For example, where the hardware modules comprise a processor 1302 configured using software, the processor 1302 may be configured as respective different hardware modules at different times. Software may accordingly configure a processor 1302, for example, to constitute a particular hardware module at one instance of time and to constitute a different hardware module at a different instance of time.

Modules can provide information to, and receive information from, other modules. For example, the described modules may be regarded as being communicatively coupled. Where multiples of such hardware modules exist contemporaneously, communications may be achieved through signal transmission (e.g., over appropriate circuits and buses) that connect the modules. In embodiments in which multiple modules are configured or instantiated at different times, communications between such modules may be achieved, for example, through the storage and retrieval of information in memory structures to which the multiple modules have access. For example, one module may perform an operation and store the output of that operation in a memory device to which it is communicatively coupled. A further module may then, at a later time, access the memory device to retrieve and process the stored output. Modules may also initiate communications with input or output devices, and can operate on a resource (e.g., a collection of information).

The various operations of example methods described herein may be performed, at least partially, by one or more processors 1302 that are temporarily configured (e.g., by software, code, and/or instructions stored in a machine-readable medium) or permanently configured to perform the relevant operations. Whether temporarily or permanently configured, such processors 1302 may constitute processor-implemented (or computer-implemented) modules that operate to perform one or more operations or functions. The modules referred to herein may, in some example embodiments, comprise processor-implemented (or computer-implemented) modules.

Moreover, the methods described herein may be at least partially processor-implemented (or computer-implemented) and/or processor-executable (or computer-executable). For example, at least some of the operations of a method may be performed by one or more processors 1302 or processor-implemented (or computer-implemented) modules. Similarly, at least some of the operations of a method may be governed by instructions that are stored in a computer readable storage medium and executed by one or more processors 1302 or processor-implemented (or computer-implemented) modules. The performance of certain of the operations may be distributed among the one or more processors 1302, not only residing within a single machine, but deployed across a number of machines. In some example embodiments, the processors 1302 may be located in a single location (e.g., within a home environment, an office environment or as a server farm), while in other embodiments the processors 1302 may be distributed across a number of locations.

While the embodiment(s) is (are) described with reference to various implementations and exploitations, it will be understood that these embodiments are illustrative and that the scope of the embodiment(s) is not limited to them. In general, techniques for the embodiments described herein may be implemented with facilities consistent with any hardware system or hardware systems defined herein. Many variations, modifications, additions, and improvements are possible.

Plural instances may be provided for components, operations or structures described herein as a single instance. Finally, boundaries between various components, operations, and data stores are somewhat arbitrary, and particular operations are illustrated in the context of specific illustrative configurations. Other allocations of functionality are envisioned and may fall within the scope of the embodiment(s). In general, structures and functionality presented as separate components in the example configurations may be implemented as a combined structure or component. Similarly, structures and functionality presented as a single component may be implemented as separate components. These and other variations, modifications, additions, and improvements fall within the scope of the embodiment(s).

The foregoing description, for purpose of explanation, has been described with reference to specific embodiments. However, the illustrative discussions above are not intended to be exhaustive or to limit the embodiments to the precise forms disclosed. Many modifications and variations are possible in view of the above teachings. The embodiments were chosen and described in order to best explain the principles and their practical applications, to thereby enable others skilled in the art to best utilize the embodiments and various embodiments with various modifications as are suited to the particular use contemplated.

What is claimed is:

1. A computer-implemented method for displaying objects in a graphical user interface of a device, the method comprising:

initiating, by a vision test module, a vision test as used by an optometrist or an ophthalmologist on the device without requiring user interaction with a graphical user interface, the vision test including presenting the vision test in the graphical user interface of the device using current display settings, the vision test including vision test objects used to test a physiological and medically based visual acuity level of a user of the device, the visual acuity level identifying visual acuity of the user;

receiving input from the user identifying the user's ability to see at least one vision test object in the vision test;

identifying, in a database, customized display settings associated with the at least one vision test object, wherein the database stores vision test objects, reference visual acuity levels, reference display settings, and a user profile for a user of the device;

changing the current display settings to the customized display settings to compensate for the visual impairment; and saving the customized display settings in persistent memory of the device for subsequent display configuration upon login by the user;

displaying, by the user interface module, further objects generated by applications running on the device with the customized display settings.

2. The computer-implemented method of claim 1, wherein presenting the vision test in the graphical user interface of the device includes:
  determining specifications of a display device for the device and a predetermined viewing distance of the display device for the device; and
  displaying the vision test objects in the graphical user interface of the device based on the specifications of the display device and the predetermined viewing distance of the display device for the device.

3. The computer-implemented method of claim 2, wherein the specifications of the display device include:
  physical dimensions of the display device; and
  a resolution of the display device.

4. The computer-implemented method of claim 2, wherein displaying the vision test objects in the graphical user interface of the device based on the specifications of the display device and the predetermined viewing distance of the display device for the device includes:
  calculating at least one scaling factor based on the specifications of the display device and the predetermined viewing distance of the display device for the device;
  scaling reference vision test objects using the at least one scaling factor, each reference vision test object corresponding to a reference visual acuity level; and
  displaying the scaled reference vision test objects in the graphical user interface of the device.

5. The computer-implemented method of claim 1, wherein identifying the display settings corresponding to the input received from the user includes:
  identifying at least one vision test object selected by the user of the device;
  determining a reference visual acuity level corresponding to the at least one vision test object;
  determining reference display settings based on the reference visual acuity level;
  determining specifications of a display device for the device and a predetermined viewing distance of the display device for the device;
  calculating at least one scaling factor based on the specifications of the display device and the predetermined viewing distance of the display device for the device; and
  scaling the reference display settings based on the at least one scaling factor to produce the display settings corresponding to the input received from the user.

6. The computer-implemented method of claim 1, wherein displaying the objects in the graphical user interface based on the display settings includes:
  scaling the objects based on the display settings; and
  displaying at least a subset of the scaled objects in a viewable area of the graphical user interface.

7. The computer-implemented method of claim 6, wherein the method further comprises placing the scaled objects that are not displayed in the viewable area in a scrollable area of the graphical user interface.

8. The computer-implemented method of claim 6, wherein the viewable area of the graphical user interface includes a viewing page, and wherein method further comprises:
  generating additional viewing pages to accommodate the scaled objects that are not displayed in the viewable area; and
  placing the scaled objects that are not displayed in the viewable area on the additional viewing pages.

9. The computer-implemented method of claim 1, wherein the objects include icons.

10. The computer-implemented method of claim 1, wherein the objects include text.

11. The computer-implemented method of claim 1, further comprising:
  detecting an end of a login session on the device; and
  restoring the display setting to display settings used prior to presenting the vision test.

12. The computer-implemented method of claim 1, further comprising:
  detecting an end of a login session on the device; and
  retaining the display settings for a future login session on the device.

13. The computer-implemented method of claim 1, wherein prior to presenting the vision test in the graphical user interface of the device, the method further comprises receiving a request from the user of the device to change display settings of the device based on the vision test.

14. The computer-implemented method of claim 13, wherein the request includes a voice-activated request.

15. The computer-implemented method of claim 13, wherein the request includes a predetermined key sequence.

16. The computer-implemented method of claim 13, wherein the request includes a predetermined gesture in the graphical user interface.

17. The computer-implemented method of claim 1, wherein the display settings are selected from the group consisting of:
  a size of an object;
  a shape of the object;
  a color of the object;
  a brightness of the object;
  a contrast level of the object; and
  a location of the object.

18. The computer-implemented method of claim 1, wherein the objects are displayed in the graphical user interface using the display settings without requiring the user to navigate through menus.

19. A system to display objects in a graphical user interface of a device, the system comprising:
  a processor,
  including a vision testing module configured to:
  initiate a vision test as used by an optometrist or an ophthalmologist on the device without requiring user interaction with the graphical user interface, the vision test including
  presenting the vision test in the graphical user interface of the device using current display settings, the vision test including vision test objects used to test a physiological and medically based visual acuity level of a user of the device, the visual acuity level identifying visual acuity of the user;
  receiving input from the user identifying the user's ability to see at least one vision test object in the vision test; and
  identifying, in a database, customized display settings associated with the at least one vision test object, wherein the database stores vision test objects, reference visual acuity levels, reference display settings and a user profile for a user of the device;
  changing the current display settings to the customized display settings to compensate for the visual impairment; and
  saving the customized display settings in persistent memory of the device for subsequent display configuration upon login by the user;

displaying, by the user interface module, further objects generated by applications running on the device with the customized display settings.

20. The system of claim 19, wherein when presenting the vision test in the graphical user interface of the device, the processor-implemented vision testing module is configured to:

determine specifications of a display device for the device and a predetermined viewing distance of the display device for the device; and display the vision test objects in the graphical user interface of the device based on the specifications of the display device and the predetermined viewing distance of the display device for the device.

21. A non-transitory computer readable storage medium storing at least one program that, when executed by at least one processor, causes the at least one processor to perform operations comprising:

initiating, by a vision test module, a vision test as used by an optometrist or an ophthalmologist on the device without requiring user interaction with a graphical user interface, the vision test including presenting the vision test in the graphical user interface of the device using current display settings, the vision test including vision test objects used to test a physiological and medically based visual acuity level of a user of the device, the visual acuity level identifying visual acuity of a user;

receiving input from the user identifying the user's ability to see at least one vision test object in the vision test;

identifying, in a database, customized display settings associated with the at least one vision test object, wherein the database stores vision test objects, reference visual acuity levels, reference display settings, and a user profile for a user of the device;

changing the current display settings to the customized display settings to compensate for the visual impairment; and saving the customized display settings in persistent memory of the device for subsequent display configuration upon login by the user;

displaying, by the user interface module, further objects generated by applications running on the device with the customized display settings.

22. The computer-implemented method of claim 1, wherein the vision test is a Snellen test.

23. The system of claim 19, wherein the vision test is a Snellen test.

24. The computer readable storage medium of claim 21, wherein the vision test is a Snellen test.

* * * * *